(12) United States Patent
    Malecha

(10) Patent No.: US 9,459,231 B2
(45) Date of Patent: *Oct. 4, 2016

(54) METHOD AND SYSTEM TO DETERMINE ERRONEOUS MEASUREMENT SIGNALS DURING A TEST MEASUREMENT SEQUENCE

(71) Applicant: LifeScan Scotland Limited, Inverness-shire (GB)

(72) Inventor: Michael Malecha, Muir of Ord (GB)

(73) Assignee: LifeScan Scotland Limited, Inverness (GB)

( * ) Notice: Subject to any disclaimer, the term of this patent is extended or adjusted under 35 U.S.C. 154(b) by 582 days.

This patent is subject to a terminal disclaimer.

(21) Appl. No.: 14/013,516

(22) Filed: Aug. 29, 2013

(65) Prior Publication Data

US 2015/0060299 A1    Mar. 5, 2015

(51) Int. Cl.
    *G01N 27/327*    (2006.01)

(52) U.S. Cl.
    CPC ...... *G01N 27/3275* (2013.01); *G01N 27/3273* (2013.01); *G01N 27/3274* (2013.01)

(58) Field of Classification Search
    CPC .................................. G01N 27/327–27/3274
    See application file for complete search history.

(56) References Cited

U.S. PATENT DOCUMENTS

| | | |
|---|---|---|
| 4,919,770 A | 4/1990 | Preidel et al. |
| 5,001,048 A | 3/1991 | Taylor et al. |
| 5,243,516 A | 9/1993 | White |
| 5,429,735 A | 7/1995 | Johnson et al. |
| 5,437,999 A | 8/1995 | Diebold et al. |
| 5,508,203 A | 4/1996 | Fuller et al. |
| 5,704,354 A | 1/1998 | Preidel et al. |
| 5,708,247 A | 1/1998 | McAleer et al. |
| 5,792,668 A | 8/1998 | Fuller et al. |
| 5,942,102 A | 8/1999 | Hodges et al. |
| 5,951,836 A | 9/1999 | McAleer et al. |
| 6,001,239 A | 12/1999 | Douglas et al. |
| 6,179,979 B1 | 1/2001 | Hodges et al. |
| 6,193,873 B1 | 2/2001 | Ohara et al. |
| 6,241,862 B1 | 6/2001 | McAleer et al. |
| 6,284,125 B1 | 9/2001 | Hodges et al. |
| 6,287,451 B1 | 9/2001 | Winarta et al. |
| 6,391,645 B1 | 5/2002 | Huang et al. |
| 6,413,410 B1 | 7/2002 | Hodges et al. |
| 6,475,372 B1 | 11/2002 | Ohara et al. |
| 6,517,482 B1 | 2/2003 | Elden et al. |
| 6,576,117 B1 | 6/2003 | Iketaki et al. |
| 6,645,368 B1 | 11/2003 | Beaty et al. |
| 6,685,633 B2 | 2/2004 | Albert et al. |

(Continued)

FOREIGN PATENT DOCUMENTS

| | | |
|---|---|---|
| AU | 738325 B2 | 9/2001 |
| EP | 749332 B1 | 3/1995 |

(Continued)

OTHER PUBLICATIONS

U.S. Appl. No. 61/530,795, McColl et al., filed Sep. 2, 2011.

(Continued)

*Primary Examiner* — Alexander Noguerola

(57) ABSTRACT

Various embodiments that allow a more accurate electrochemical test strip measurement by identifying erroneous output signals during a glucose measurement thereby ensuring a much more accurate glucose test system.

10 Claims, 9 Drawing Sheets

(56) References Cited

U.S. PATENT DOCUMENTS

| | | |
|---|---|---|
| 6,716,577 B1 | 4/2004 | Yu et al. |
| 6,733,655 B1 | 5/2004 | Davies et al. |
| 6,749,887 B1 | 6/2004 | Dick et al. |
| 6,767,441 B1 | 7/2004 | Cai et al. |
| 6,780,645 B2 | 8/2004 | Hayter et al. |
| 6,841,389 B2 | 1/2005 | Novikov et al. |
| 6,863,801 B2 | 3/2005 | Hodges et al. |
| 6,890,421 B2 | 5/2005 | Ohara et al. |
| 7,018,843 B2 | 3/2006 | Heller |
| 7,045,046 B2 | 5/2006 | Chambers et al. |
| 7,050,847 B2 | 5/2006 | Ollmar et al. |
| 7,258,769 B2 | 8/2007 | Cui et al. |
| 7,291,256 B2 | 11/2007 | Teodorczyk et al. |
| 7,338,639 B2 | 3/2008 | Burke et al. |
| 7,390,667 B2 | 6/2008 | Burke et al. |
| 7,407,811 B2 | 8/2008 | Burke et al. |
| 7,452,457 B2 | 11/2008 | Burke et al. |
| 7,488,601 B2 | 2/2009 | Burke et al. |
| 7,494,816 B2 | 2/2009 | Burke et al. |
| 7,498,132 B2 | 3/2009 | Yu et al. |
| 7,597,793 B2 | 10/2009 | Burke et al. |
| 7,601,249 B2 | 10/2009 | Iyengar et al. |
| 7,604,721 B2 | 10/2009 | Groll et al. |
| 7,645,373 B2 | 1/2010 | Groll et al. |
| 7,645,421 B2 | 1/2010 | Groll |
| 7,678,250 B2 | 3/2010 | Bell et al. |
| 7,718,439 B2 | 5/2010 | Groll |
| 7,727,467 B2 | 6/2010 | Burke et al. |
| 7,749,371 B2 * | 7/2010 | Guo ............... A61B 5/14532 205/775 |
| 7,749,437 B2 | 7/2010 | Mosoiu et al. |
| 7,751,864 B2 | 7/2010 | Buck, Jr. |
| 7,829,023 B2 | 11/2010 | Burke et al. |
| 7,879,618 B2 | 2/2011 | Mosoiu et al. |
| 7,892,849 B2 | 2/2011 | Burke et al. |
| 7,923,258 B2 | 4/2011 | Heller |
| 7,927,882 B2 | 4/2011 | Heller |
| 7,955,492 B2 | 6/2011 | Fujiwara et al. |
| 7,964,089 B2 | 6/2011 | Harding et al. |
| 7,972,851 B2 | 7/2011 | Wang et al. |
| 7,972,861 B2 | 7/2011 | Deng et al. |
| 8,080,153 B2 | 12/2011 | Feldman et al. |
| 8,083,925 B2 | 12/2011 | Feldman et al. |
| 8,088,271 B2 | 1/2012 | Fujiwara et al. |
| 8,148,164 B2 | 4/2012 | Diebold et al. |
| 8,163,162 B2 | 4/2012 | Chatelier et al. |
| 8,409,424 B2 | 4/2013 | Chen et al. |
| 8,623,660 B2 | 1/2014 | Kraft et al. |
| 2004/0005716 A9 | 1/2004 | Beaty et al. |
| 2004/0079652 A1 | 4/2004 | Vreeke et al. |
| 2004/0157339 A1 | 8/2004 | Burke et al. |
| 2007/0084734 A1 | 4/2007 | Roberts et al. |
| 2007/0087397 A1 | 4/2007 | Kraft et al. |
| 2007/0227912 A1 | 10/2007 | Chatelier et al. |
| 2008/0083618 A1 | 4/2008 | Neel et al. |
| 2008/0274447 A1 | 11/2008 | Mecklenburg |
| 2009/0177406 A1 | 7/2009 | Wu |
| 2009/0194432 A1 | 8/2009 | Deng |
| 2009/0223834 A1 | 9/2009 | Cai et al. |
| 2009/0236237 A1 | 9/2009 | Shinno et al. |
| 2010/0005865 A1 | 1/2010 | Miura |
| 2010/0089775 A1 | 4/2010 | Chen et al. |
| 2010/0170807 A1 | 7/2010 | Diebold et al. |
| 2010/0206749 A1 | 8/2010 | Choi |
| 2010/0276303 A1 | 11/2010 | Fujiwara et al. |
| 2010/0283488 A1 | 11/2010 | Nakamura et al. |
| 2010/0320097 A1 | 12/2010 | Miyazaki et al. |
| 2011/0030093 A1 | 2/2011 | Dhugga |
| 2011/0036729 A1 | 2/2011 | Matsuda et al. |
| 2011/0168575 A1 | 7/2011 | Lica et al. |
| 2011/0294554 A1 | 12/2011 | Barratt et al. |
| 2011/0297554 A1 | 12/2011 | Wu et al. |
| 2011/0297557 A1 | 12/2011 | Wu et al. |
| 2011/0301857 A1 | 12/2011 | Huang et al. |
| 2012/0031777 A1 | 2/2012 | Burke et al. |
| 2012/0043227 A1 | 2/2012 | Miyazaki et al. |
| 2012/0129423 A1 | 5/2012 | Finizza |
| 2013/0337571 A1 | 12/2013 | Mizuoka et al. |

FOREIGN PATENT DOCUMENTS

| | | |
|---|---|---|
| EP | 691539 B1 | 6/1995 |
| EP | 1394545 A1 | 3/2004 |
| EP | 1828759 B1 | 10/2005 |
| EP | 1804048 B1 | 12/2005 |
| EP | 1042667 B1 | 6/2009 |
| WO | WO 9932881 A1 | 7/1999 |
| WO | WO 2006040200 A1 | 4/2006 |
| WO | WO 2006/070200 A1 | 7/2006 |
| WO | WO 2008/036516 A1 | 3/2008 |
| WO | WO 2008/040998 A2 | 4/2008 |
| WO | WO 2008/049075 A2 | 4/2008 |
| WO | WO 2010/049669 A1 | 5/2010 |
| WO | WO 2011/121292 A1 | 10/2011 |
| WO | WO 2012/091728 A1 | 7/2012 |
| WO | WO 2012/153535 A1 | 11/2012 |

OTHER PUBLICATIONS

U.S. Appl. No. 61/530,808, McColl et al., filed Sep. 2, 2011.
U.S. Appl. No. 61/581,087, Malecha et al., filed Dec. 29, 2011.
U.S. Appl. No. 61/581,089, Malecha et al., filed Dec. 29, 2011.
U.S. Appl. No. 61/581,099, Malecha et al., filed Dec. 29, 2011.
U.S. Appl. No. 61/581,100, Smith et al., filed Dec. 29, 2011.
U.S. Appl. No. 61/654,013, Malecha et al., filed May 31, 2012.
International Application No. PCT/GB2012/053276, PCT International Search Report and Written Opinion, 13 pages, dated May 3, 2013.
International Application No. PCT/GB2012/053277, PCT International Search Report and Written Opinion, 13 pages, dated May 3, 2013.
International Application No. PCT/GB2012/053279, PCT International Search Report and Written Opinion, 13 pages, dated May 3, 2013.
Patent Examination Report issued in related Australian Patent Application No. 2012327229, May 28, 2014, 5 pages.
Wegener, Joachim et al., "Electric Cell—Substrate Impedance Sensing (ECIS) as a Noninvasive Means to Monitor the Kinetics of Cell Spreading to Artificial Surfaces," Experimental Cell Research 259, 158-166 (2000) doi:10.1006/excr.2000.4919, available online at http://www.idealibrary.coml.
Kohma, Takuya et al., "Utilization of AC Impedance Measurements for Electrochemical Glucose Sensing Using Glucose Oxidase to Improve Detection Selectivity," Bull. Chem. Soc. Jpn. vol. 80, No. 1, 158-165 (2007).
Baskurt, Oguz K. et al., "Blood Rheology and Hemodynamics," Seminars in Thrombosis and Hemostasis, vol. 29, No. 5, 2003.
Nordbotten, Bernt, J. et al., "Methods for calculating phase angle from measured whole body bioimpedance modulus.".
Wang, J. et al., "Electrochemical Impedance Biosensor for Glucose Detection Utilizing a Periplasmic E. coli Receptor Protein," Electrochemical and Solid-State Letters, 8 (8) H61-H64 (2005).
Caduff, A. et al., "First human experiments with a novel non-invasive, non-optical continuous glucose monitoring system," Biosensors and Bioelectronics 19 (2003) 209-217.
Guevara, Edgar et al., "Prediction of Glucose Concentration by Impedance Phase Measurements," CP1032, Medical Physics—Tenth Symposium of Medical Physics, 2008 American Institute of Physics 978-0-7354-0556, 259-261.
Park, J.-H. et al., "The correlation of the complex dielectric constant and blood glucose at low frequency," Biosensors and Bioelectronics 19 (2003) 321-324.
De Vries, P.M.J.M. et al., "Implications of the dielectrical behavior of human blood for continuous online measurement of haematocrit," Med. & Biol. Eng. & Comput. 1993, 31, 445-448.
"Annex A—Bioimpedance monitoring for physicians: an overview," pp. 131-178.
Koschinsky, T. et al., "Sensors for glucose monitoring: technical and clinical aspects," Diabetes Metab Res Rev 2001; 17: 113-123.

(56) References Cited

OTHER PUBLICATIONS

Marks, Vincent, "Blood glucose: its measurement and clinical importance," Clinica Chimica Acta 251 (1996) 3-17.
Shervedani, Reza Karimi et al., "A novel method for glucose determination based on electrochemical impedance spectroscopy using glucose oxidase self-assembled biosensor," Bioelectrochemistry 69 (2006) 201-208.
Tura, Andrea et al., "Non-invasive glucose monitoring: Assessment of technologies and devices according to quantitative criteria," Diabetes Research and Clinical Practice 77 (2007) 16-40.
Tierney, M.J. et al., "Clinical evaluation of the GlucoWatch® biographer: a continual, non-invasive glucose monitor for patients with diabetes," Biosensors & Bioelectronics 16 (2001) 621-629.
Tura, A. et al., "Impedance spectroscopy of solutions at physiological glucose concentrations," Biophysical Chemistry 129 (2007) 235-241.
International Preliminary Report on Patentability issued in related International Patent Application No. PCT/GB2012/053279, issued Jul. 1, 2004, 10 pages.
Patent Examination Report issued in related Australian Patent Application No. 2012340500, issued Aug. 4, 2014, 3 pages.
International Preliminary Report on Patentability issued in related International Patent Application No. PCT/GB2012/053277, issued Jul. 1, 2004, 11 pages.
International Preliminary Report on Patentability issued in related International Patent Application No. PCT/GB2012/053276, issued Jul. 1, 2004, 11 pages.
International Search Report and Written Opinion issued in related International Patent Application No. PCT/EP2014/068318, mailed Nov. 17, 2014, 13 pages.

\* cited by examiner

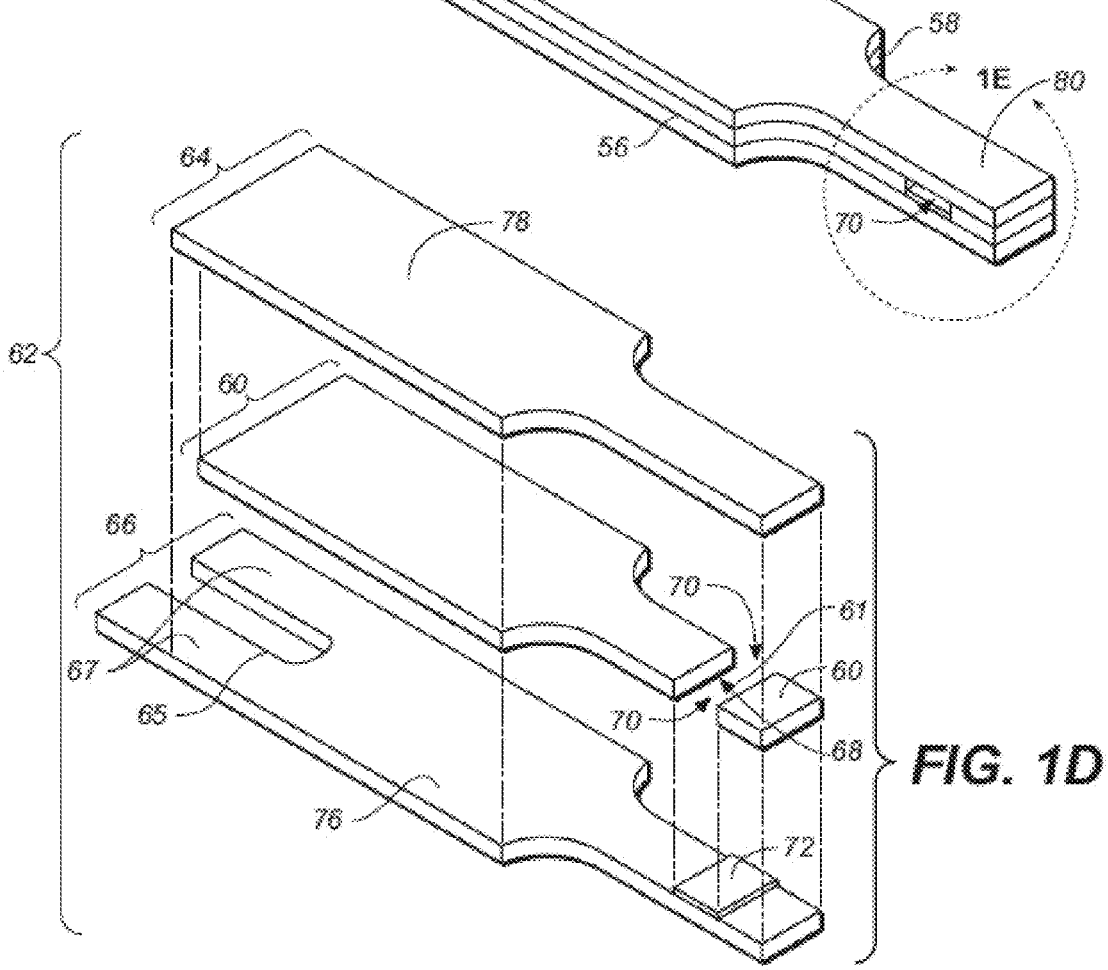
FIG. 1C
FIG. 1D
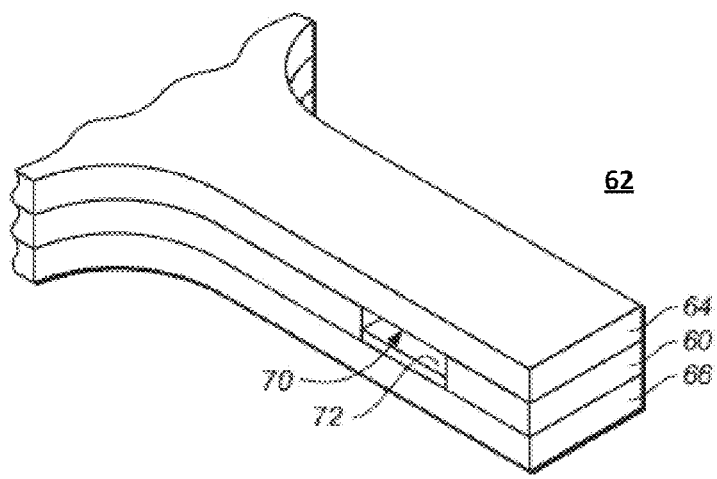
FIG. 1E

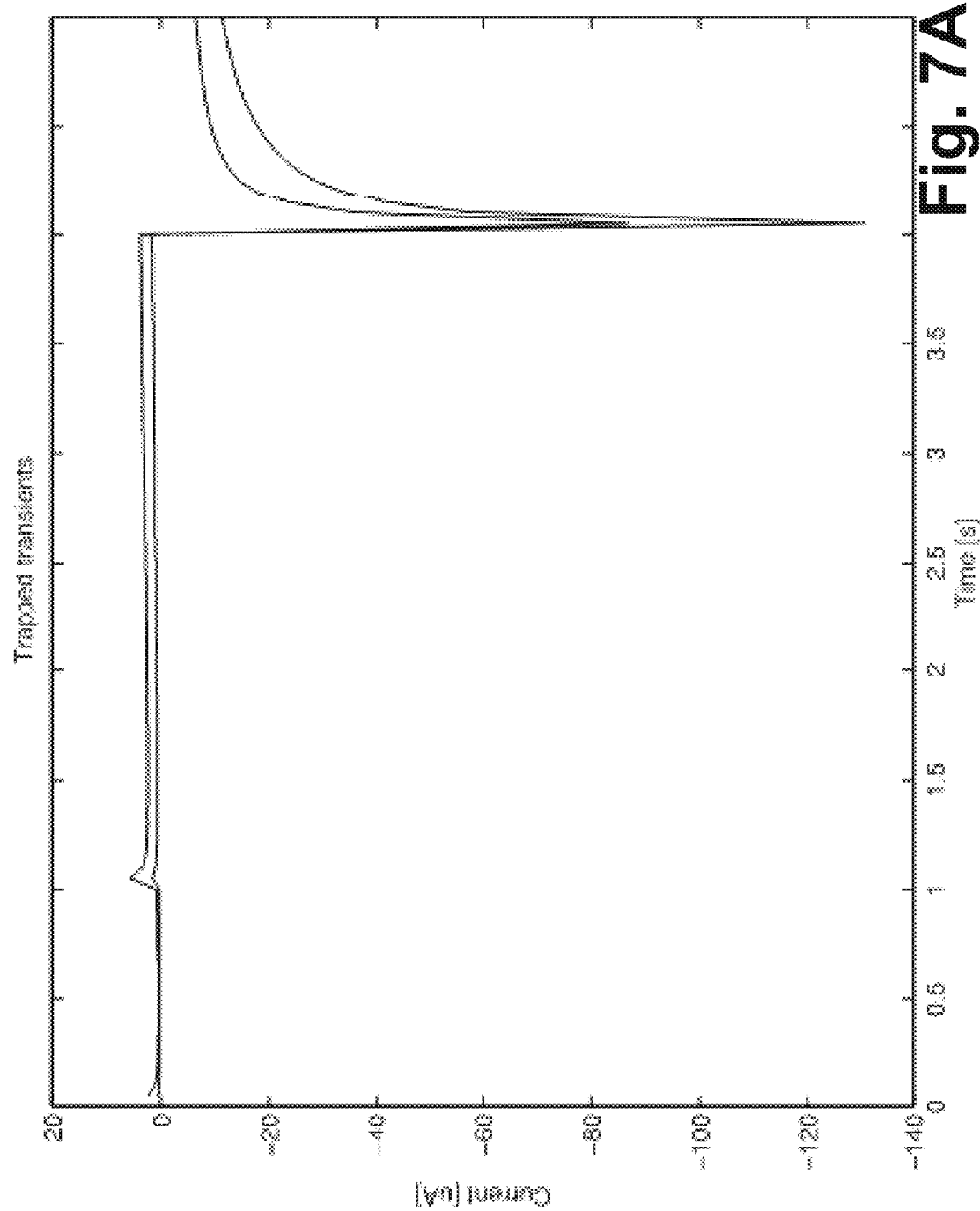

METHOD AND SYSTEM TO DETERMINE ERRONEOUS MEASUREMENT SIGNALS DURING A TEST MEASUREMENT SEQUENCE

BACKGROUND

Electrochemical glucose test strips, such as those used in the OneTouch® Ultra® whole blood testing kit, which is available from LifeScan, Inc., are designed to measure the concentration of glucose in a blood sample from patients with diabetes. The measurement of glucose can be based on the selective oxidation of glucose by the enzyme glucose oxidase (GO). The reactions that can occur in a glucose test strip are summarized below in Equations 1 and 2.

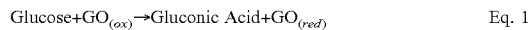
$$\text{Glucose} + GO_{(ox)} \rightarrow \text{Gluconic Acid} + GO_{(red)} \quad \text{Eq. 1}$$

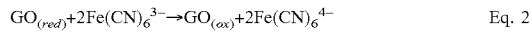
$$GO_{(red)} + 2Fe(CN)_6^{3-} \rightarrow GO_{(ox)} + 2Fe(CN)_6^{4-} \quad \text{Eq. 2}$$

As illustrated in Equation 1, glucose is oxidized to gluconic acid by the oxidized form of glucose oxidase ($GO_{(ox)}$). It should be noted that $GO_{(ox)}$ may also be referred to as an "oxidized enzyme." During the reaction in Equation 1, the oxidized enzyme $GO_{(ox)}$ is converted to its reduced state, which is denoted as $GO_{(red)}$ (i.e., "reduced enzyme"). Next, the reduced enzyme $GO_{(red)}$ is re-oxidized back to $GO_{(ox)}$ by reaction with $Fe(CN)_6^{3-}$ (referred to as either the oxidized mediator or ferricyanide) as illustrated in Equation 2. During the re-generation of $GO_{(red)}$ back to its oxidized state $GO_{(ox)}$, $Fe(CN)_6^{3-}$ is reduced to $Fe(CN)_6^{4-}$ (referred to as either reduced mediator or ferrocyanide).

When the reactions set forth above are conducted with a test voltage applied between two electrodes, a test output signal can be created by the electrochemical re-oxidation of the reduced mediator at the electrode surface. Thus, since, in an ideal environment, the amount of ferrocyanide created during the chemical reaction described above is directly proportional to the amount of glucose in the sample positioned between the electrodes, the test output signal generated would be proportional to the glucose content of the sample. A mediator, such as ferricyanide, is a compound that accepts electrons from an enzyme such as glucose oxidase and then donates the electrons to an electrode. As the concentration of glucose in the sample increases, the amount of reduced mediator formed also increases; hence, there is a direct relationship between the test output signal, resulting from the re-oxidation of reduced mediator, and glucose concentration. In particular, the transfer of electrons across the electrical interface results in the flow of a test output signal (2 moles of electrons for every mole of glucose that is oxidized). The test output signal resulting from the introduction of glucose can, therefore, be referred to as a glucose output signal.

Because it can be very important to know the concentration of glucose in blood, particularly in people with diabetes, test meters have been developed using the principals set forth above to enable the average person to sample and test their blood for determining their glucose concentration at any given time. The glucose output signal generated is detected by the test meter and converted into a glucose concentration reading using an algorithm that relates the test output signal to a glucose concentration via a simple mathematical formula. In general, the test meters work in conjunction with a disposable test strip that may include a sample-receiving chamber and at least two electrodes disposed within the sample-receiving chamber in addition to the enzyme (e.g. glucose oxidase) and the mediator (e.g. ferricyanide). In use, the user pricks their finger or other convenient site to induce bleeding and introduces a blood sample to the sample-receiving chamber, thus starting the chemical reaction set forth above.

SUMMARY OF THE DISCLOSURE

In one aspect, applicants have devised a glucose measurement system that includes at least one biosensor and a meter. The biosensor has a plurality of electrodes including at least two electrodes with a reagent disposed thereon. The meter includes a microcontroller coupled to a power source, memory and the plurality of electrodes of the biosensor. In this system, the microcontroller is configured to: drive a signal to the at least two electrodes when a fluid sample with an glucose is deposited proximate the at least two electrodes to start a test measurement sequence for an electrochemical reaction of the glucose in the fluid sample with the reagent; measure an output signal from at least one electrode during the electrochemical reaction over a series of time intervals to obtain a magnitude of the output signal for each time interval (i); determine an output differential as a difference in the respective magnitudes of the output signal for at least two consecutive time intervals within a predetermined time window during the test measurement sequence; if the output differential is greater than a predetermined threshold then increment an index value as equal to the sum of both a previous value of the index and the output differential and if the index is greater or equal to a predetermined index value then annunciate an error otherwise calculate the glucose value from the output signal and annunciate the glucose value.

In yet another aspect, a method of determining a glucose value from a fluid sample with a system is provided by applicant. The system includes a biosensor having at least two electrodes and reagent disposed thereon and a glucose meter having a microcontroller configured to connect to the biosensor and to a memory and a power source. The method can be achieved by: initiating a start of a test measurement sequence upon deposition of a fluid sample proximate the at least two electrodes of the biosensor; applying an input signal to the fluid sample to cause a transformation of glucose into an enzymatic by-product; measuring output signal transient from the fluid sample over a predetermined time window from the start of the test sequence, the measuring including sampling an output signal from at least one electrode during the electrochemical reaction over a series of time intervals to obtain a magnitude of the output signal for each time interval; determining an output differential as a difference in the respective magnitudes of the output signal for at least two consecutive time intervals within the predetermined time window during the test measurement sequence; if the output differential is greater than zero then setting an index value as equal to the sum of both a previous value of the index and the output differential otherwise if the index is greater than a predetermined index value then annunciating an error, otherwise calculating a glucose value of the fluid sample and annunciating the glucose value.

And for these aspects, the following features may also be utilized in various combinations with these previously disclosed aspects: the predetermined time window comprises from about 1 second after a start of a test sequence to about 8 seconds after the start of the test sequence; the predetermined index value comprises about 2 microamps and the predetermined threshold comprises about 0.5 microamps; the predetermined time window comprises from about 2 seconds after the start of a test sequence to about 8 seconds after the start of the test sequence; the predetermined index value comprises about 5 and the predetermined threshold comprises about 150; the calculating of the glucose value comprises measuring a magnitude of the output signal proximate a predetermined time interval from the start of the test sequence and utilizing an equation of the form:

These and other embodiments, features and advantages will become apparent to those skilled in the art when taken with reference to the following more detailed description of the exemplary embodiments of the invention in conjunction with the accompanying drawings that are first briefly described.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention (wherein like numerals represent like elements), in which:

FIG. 1C illustrates a perspective view of an assembled test strip suitable for use in the system and methods disclosed herein;

FIG. 1D illustrates an exploded perspective view of an unassembled test strip suitable for use in the system and methods disclosed herein;

FIG. 1E illustrates an expanded perspective view of a proximal portion of the test strip suitable for use in the system and methods disclosed herein;

FIG. 7A illustrates transient signal outputs that may be erroneous and therefore unsuitable for analyte assay.

MODES OF CARRYING OUT THE INVENTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±10% of the recited value, e.g. "about 90%" may refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment. As used herein, "oscillating signal" includes voltage signal(s) or current signal(s) that, respectively, change polarity or alternate direction of current or are multi-directional. Also used herein, the phrase "electrical signal" or "signal" is intended to include direct current signal, alternating signal or any signal within the electromagnetic spectrum. The terms "processor"; "microprocessor"; or "microcontroller" are intended to have the same meaning and are intended to be used interchangeably.

Figure 1A:
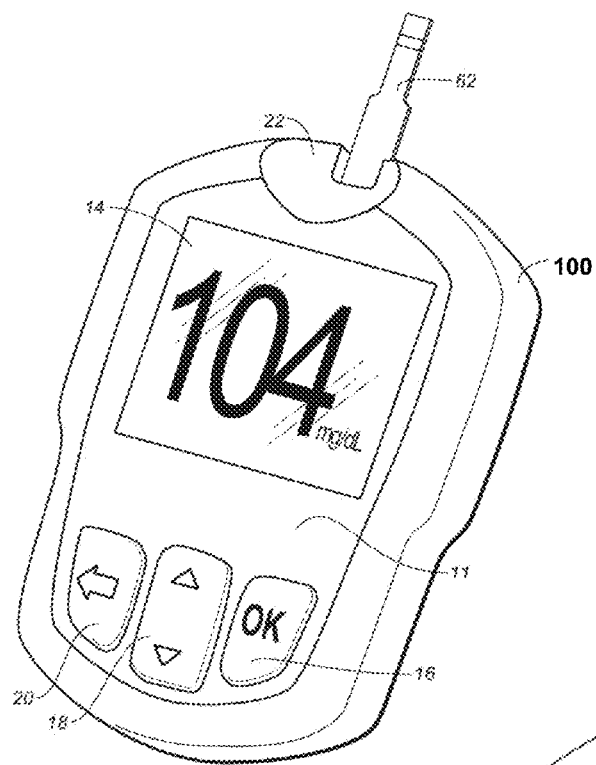
FIG. 1A illustrates a preferred blood glucose measurement system.

FIG. 1A illustrates a diabetes management system that includes a meter 10 and a biosensor in the form of a glucose test strip 62. Note that the meter (meter unit) may be referred to as an analyte measurement and management unit, a glucose meter, a meter, and an analyte measurement device. In an embodiment, the meter unit may be combined with an insulin delivery device, an additional analyte testing device, and a drug delivery device. The meter unit may be connected to a remote computer or remote server via a cable or a suitable wireless technology such as, for example, GSM, CDMA, BlueTooth, WiFi and the like.

Referring back to FIG. 1A, glucose meter or meter unit 10 may include a housing 11, user interface buttons (16, 18, and 20), a display 14, and a strip port opening 22. User interface buttons (16, 18, and 20) may be configured to allow the entry of data, navigation of menus, and execution of commands. User interface button 18 may be in the form of a two way toggle switch. Data may include values representative of analyte concentration, and/or information, which are related to the everyday lifestyle of an individual. Information, which is related to the everyday lifestyle, may include food intake, medication use, occurrence of health check-ups, and general health condition and exercise levels of an individual. The electronic components of meter 10 may be disposed on a circuit board 34 that is within housing 11.

Figure 1B:
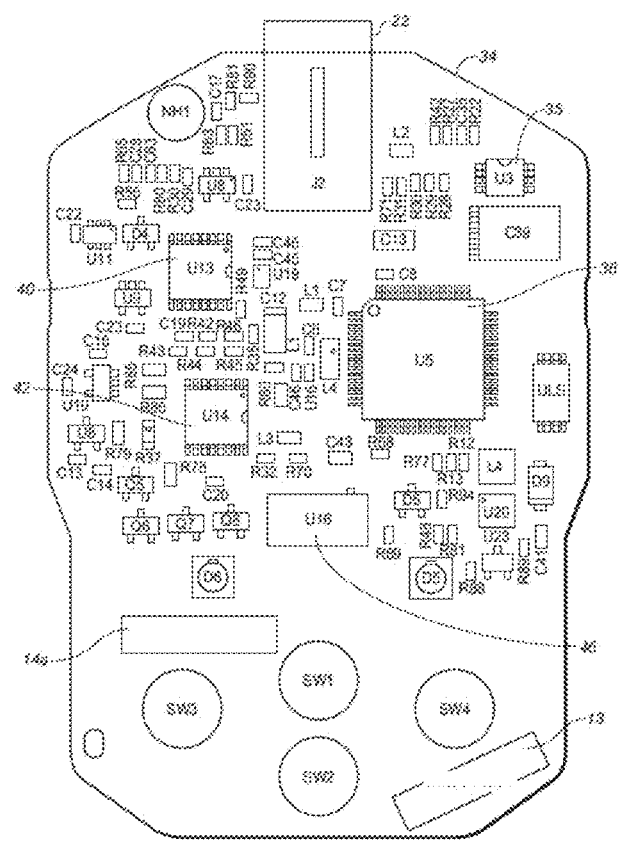
FIG. 1B illustrates the various components disposed in the meter of FIG. 1A.

FIG. 1B illustrates (in simplified schematic form) the electronic components disposed on a top surface of circuit board 34. On the top surface, the electronic components include a strip port connector 22, an operational amplifier circuit 35, a microcontroller 38, a display connector 14a, a non-volatile memory 40, a clock 42, and a first wireless module 46. On the bottom surface, the electronic components may include a battery connector (not shown) and a data port 13. Microcontroller 38 may be electrically connected to strip port connector 22, operational amplifier circuit 35, first wireless module 46, display 14, non-volatile memory 40, clock 42, battery, data port 13, and user interface buttons (16, 18, and 20).

Operational amplifier circuit 35 may include two or more operational amplifiers configured to provide a portion of the potentiostat function and the signal measurement function. The potentiostat function may refer to the application of a test voltage between at least two electrodes of a test strip. The current function may refer to the measurement of a test signal resulting from the applied test voltage. The signal measurement may be performed with a current-to-voltage converter. Microcontroller 38 may be in the form of a mixed signal microprocessor (MSP) such as, for example, the Texas Instrument MSP 430. The TI-MSP 430 may be configured to also perform a portion of the potentiostat function and the signal measurement function. In addition, the MSP 430 may also include volatile and non-volatile memory. In another embodiment, many of the electronic components may be integrated with the microcontroller in the form of an application specific integrated circuit (ASIC).

Strip port connector 22 may be configured to form an electrical connection to the test strip. Display connector 14a may be configured to attach to display 14. Display 14 may be in the form of a liquid crystal display for reporting measured glucose levels, and for facilitating entry of lifestyle related information. Display 14 may optionally include a backlight. Data port 13 may accept a suitable connector attached to a connecting lead, thereby allowing glucose meter 10 (or 100) to be linked to an external device such as a personal computer. Data port 13 may be any port that allows for transmission of data such as, for example, a serial, USB, or a parallel port. Clock 42 may be configured to keep current time related to the geographic region in which the user is located and also for measuring time. The meter unit may be configured to be electrically connected to a power supply such as, for example, a battery.

Figures 2, 3, 4A:
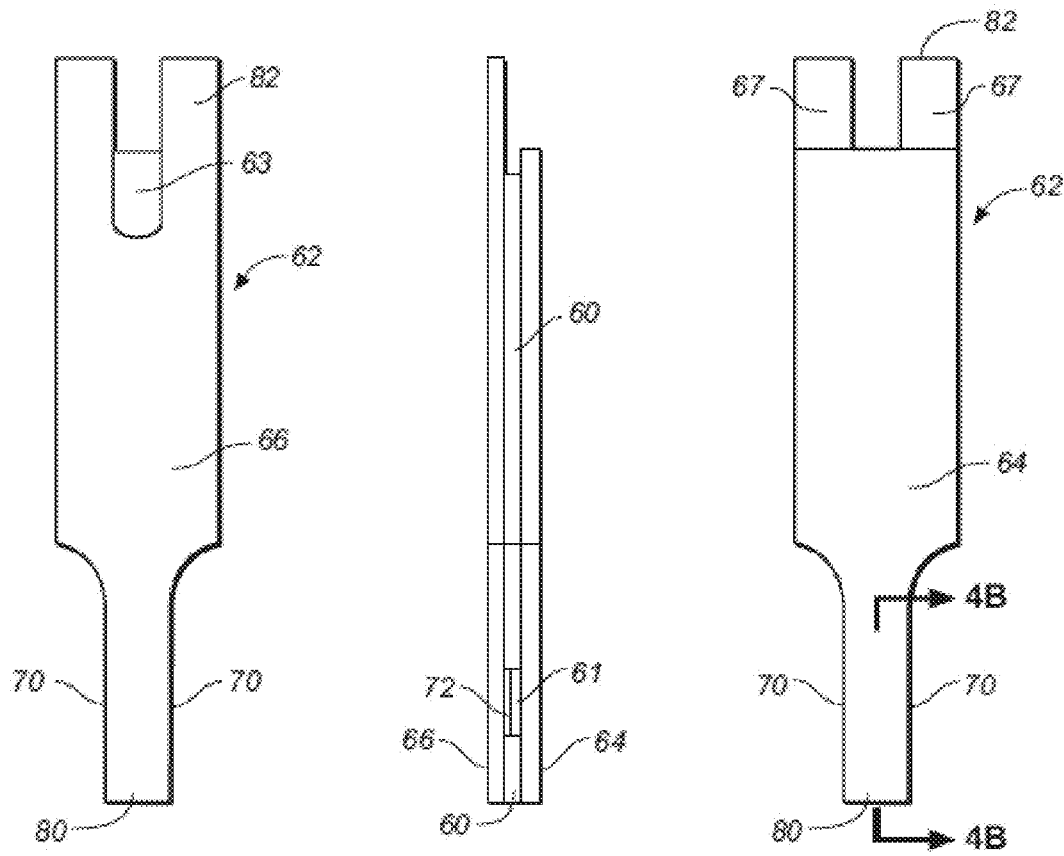
FIG. 2 illustrates a bottom plan view of one embodiment of a test strip disclosed herein.
FIG. 3 illustrates a side plan view of the test strip of FIG. 2.
FIG. 4A illustrates a top plan view of the test strip of FIG. 3.
Figure 4B:
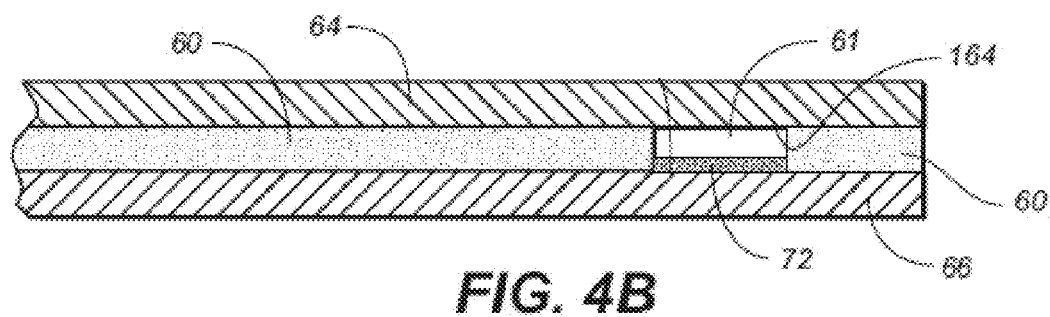
FIG. 4B illustrates a partial side view of a proximal portion of the test strip of FIG. 4A.

FIGS. 1C-1E, 2, 3, and 4B show various views of an exemplary test strip 62 suitable for use with the methods and systems described herein. In an exemplary embodiment, a test strip 62 is provided which includes an elongate body extending from a distal end 80 to a proximal end 82, and having lateral edges 56, 58, as illustrated in FIG. 1C. As shown in FIG. 1D, the test strip 62 also includes a first electrode layer 66, a second electrode layer 64, and a spacer 60 sandwiched in between the two electrode layers 64 and 66. The first electrode layer 66 may include a first electrode 66, a first connection track 76, and a first contact pad 67, where the first connection track 76 electrically connects the first electrode 66 to the first contact pad 67, as shown in FIGS. 1D and 4B. Note that the first electrode 66 is a portion of the first electrode layer 66 that is immediately underneath the reagent layer 72, as indicated by FIGS. 1D and 4B. Similarly, the second electrode layer 64 may include a second electrode 64, a second connection track 78, and a second contact pad 63, where the second connection track 78 electrically connects the second electrode 64 with the second contact pad 63, as shown in FIGS. 1D, 2, and 4B. Note that the second electrode 64 is a portion of the second electrode layer 64 that is above the reagent layer 72, as indicated by FIG. 4B. As used herein, the terms "electrode layer" and "electrode" are used interchangeably to refer to the general area encompassing an electrode or a specific location for the electrode. Also, the reagent includes both the enzymes and other materials such as binders and other materials to allow the reagent to function for its intended purpose in a biosensor.

As shown, the sample-receiving chamber 61 is defined by the first electrode 66, the second electrode 64, and the spacer 60 near the distal end 80 of the test strip 62, as shown in FIG. 1C. The first electrode 66 and the second electrode 64 may define the bottom and the top of sample-receiving chamber 61, respectively, as illustrated in FIG. 4B. A cutout area 68 of the spacer 60 may define the sidewalls of the sample-receiving chamber 61, as illustrated in FIG. 1D. In one aspect, the sample-receiving chamber 61 may include ports 70 that provide a sample inlet and/or a vent, as shown in FIGS. 1C to 1E. For example, one of the ports may allow a fluid sample to ingress and the other port may allow air to egress.

In an exemplary embodiment, the sample-receiving chamber 61 (or test cell or test chamber) may have a small volume. For example, the chamber 61 may have a volume in the range of from about 0.1 microliters to about 5 microliters, about 0.2 microliters to about 3 microliters, or, preferably, about 0.3 microliters to about 1 microliter. To provide the small sample volume, the cutout 68 may have an area ranging from about 0.01 $cm^2$ to about 0.2 $cm^2$, about 0.02 $cm^2$ to about 0.15 $cm^2$, or, preferably, about 0.03 $cm^2$ to about 0.08 $cm^2$. In addition, first electrode 66 and second electrode 64 may be spaced apart in the range of about 1 micron to about 500 microns, preferably between about 10 microns and about 400 microns, and more preferably between about 40 microns and about 200 microns. The relatively close spacing of the electrodes may also allow redox cycling to occur, where oxidized mediator generated at first electrode 66, may diffuse to second electrode 64 to become reduced, and subsequently diffuse back to first electrode 66 to become oxidized again. Those skilled in the art will appreciate that various such volumes, areas, and/or spacing of electrodes is within the spirit and scope of the present disclosure.

In one embodiment, the first electrode layer 66 and the second electrode layer 64 may be a conductive material formed from materials such as gold, palladium, carbon, silver, platinum, tin oxide, iridium, indium, or combinations thereof (e.g., indium doped tin oxide). In addition, the electrodes may be formed by disposing a conductive material onto an insulating sheet (not shown) by a sputtering, electroless plating, or a screen-printing process. In one exemplary embodiment, the first electrode layer 66 and the second electrode layer 64 may be made from sputtered palladium and sputtered gold, respectively. Suitable materials that may be employed as spacer 60 include a variety of insulating materials, such as, for example, plastics (e.g., PET, PETG, polyimide, polycarbonate, polystyrene), silicon, ceramic, glass, adhesives, and combinations thereof. In one embodiment, the spacer 60 may be in the form of a double sided adhesive coated on opposing sides of a polyester sheet where the adhesive may be pressure sensitive or heat activated. Applicants note that various other materials for the first electrode layer 66, the second electrode layer 64, and/or the spacer 60 are within the spirit and scope of the present disclosure.

Either the first electrode 66 or the second electrode 64 may perform the function of a working electrode depending on the magnitude and/or polarity of the applied test voltage. The working electrode may measure a limiting test signal that is proportional to the reduced mediator concentration. For example, if the signal limiting species is a reduced mediator (e.g., ferrocyanide), then it may be oxidized at the first electrode 66 as long as the test voltage is sufficiently greater than the redox mediator potential with respect to the second electrode 64. In such a situation, the first electrode 66 performs the function of the working electrode and the second electrode 64 performs the function of a counter/reference electrode. Applicants note that one may refer to a counter/reference electrode simply as a reference electrode or a counter electrode. A limiting oxidation occurs when all reduced mediator has been depleted at the working electrode surface such that the measured oxidation current is proportional to the flux of reduced mediator diffusing from the bulk solution towards the working electrode surface. The term "bulk solution" refers to a portion of the solution sufficiently far away from the working electrode where the reduced mediator is not located within a depletion zone. It should be noted that unless otherwise stated for test strip 62, all potentials applied by test meter 10 (or 100) will hereinafter be stated with respect to second electrode 64.

Similarly, if the test voltage is sufficiently less than the redox mediator potential, then the reduced mediator may be oxidized at the second electrode 64 as a limiting current. In such a situation, the second electrode 64 performs the function of the working electrode and the first electrode 66 performs the function of the counter/reference electrode.

Initially, an analysis may include introducing a quantity of a fluid sample into a sample-receiving chamber 61 via a port 70. In one aspect, the port 70 and/or the sample-receiving chamber 61 may be configured such that capillary action causes the fluid sample to fill the sample-receiving chamber 61. The first electrode 66 and/or second electrode 64 may be coated with a hydrophilic reagent to promote the capillarity of the sample-receiving chamber 61. For example, thiol derivatized reagents having a hydrophilic moiety such as 2-mercaptoethane sulfonic acid may be coated onto the first electrode and/or the second electrode.

In the analysis of strip 62 above, reagent layer 72 can include glucose dehydrogenase (GDH) based on the PQQ co-factor and ferricyanide. In another embodiment, the enzyme GDH based on the PQQ co-factor may be replaced with the reagent GDH based on the FAD co-factor. When blood or control solution is dosed into a sample reaction chamber 61, glucose is oxidized by $GDH_{(ox)}$ and in the process converts $GDH_{(ox)}$ to $GDH_{(red)}$, as shown in the chemical transformation T.1 below. Note that $GDH_{(ox)}$ refers to the oxidized state of GDH, and $GDH_{(red)}$ refers to the reduced state of GDH.

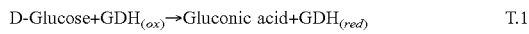

$$D\text{-Glucose} + GDH_{(ox)} \rightarrow \text{Gluconic acid} + GDH_{(red)} \quad \text{T.1}$$

Next, $GDH_{(red)}$ regenerated back to its active oxidized state by ferricyanide (i.e. oxidized mediator or $Fe(CN)_6^{3-}$) as shown in chemical transformation T.2 below. In the process of regenerating $GDH_{(ox)}$, ferrocyanide (i.e. reduced mediator or $Fe(CN)_6^{4-}$) is generated from the reaction as shown in T.2:

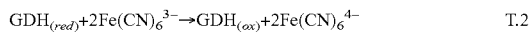

$$GDH_{(red)} + 2Fe(CN)_6^{3-} \rightarrow GDH_{(ox)} + 2Fe(CN)_6^{4-} \quad \text{T.2}$$

Figure 5:
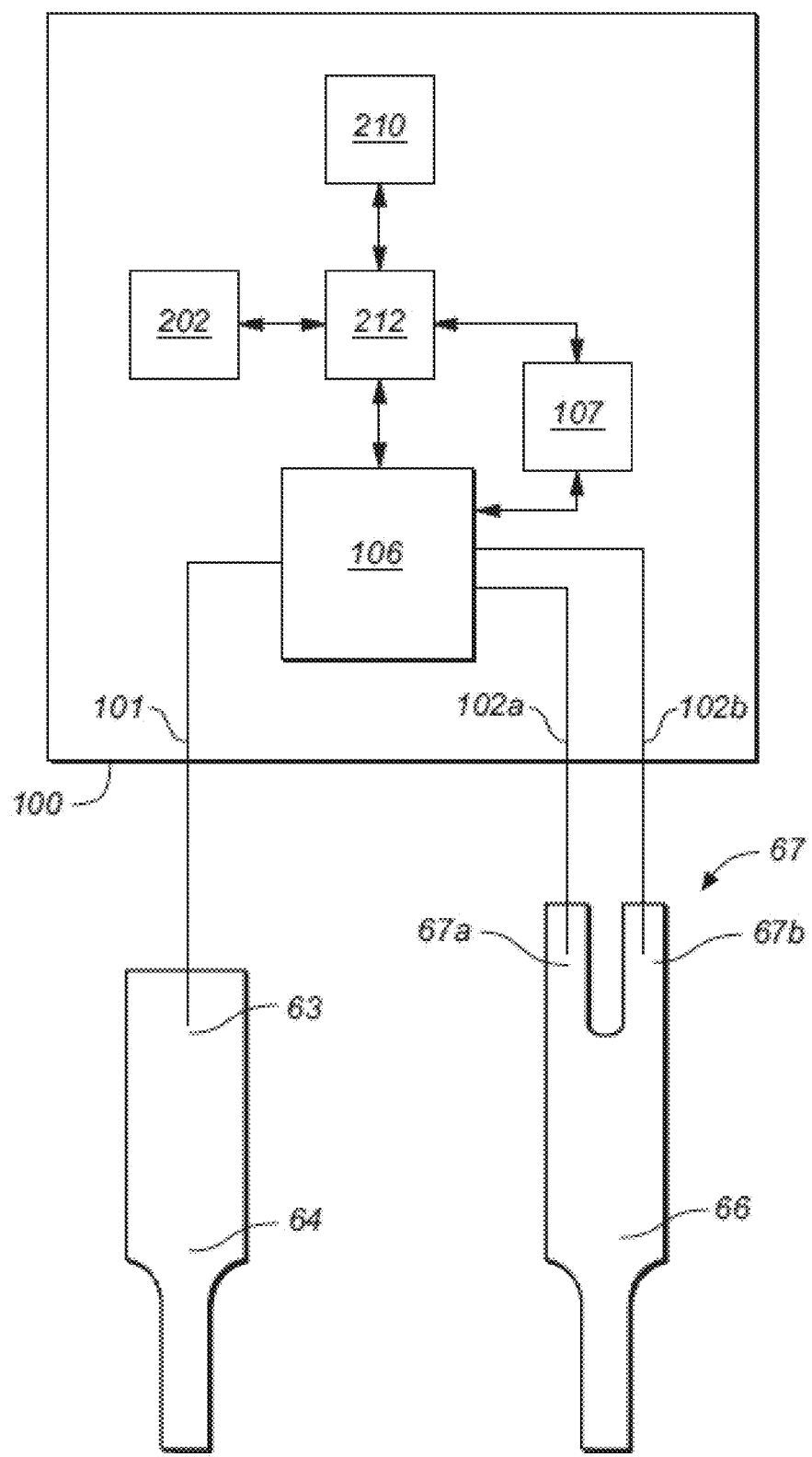
FIG. 5 illustrates a simplified schematic showing a test meter electrically interfacing with portions of a test strip disclosed herein.

FIG. 5 provides a simplified schematic showing a test meter 100 interfacing with a first contact pad 67a, 67b and a second contact pad 63. The second contact pad 63 may be used to establish an electrical connection to the test meter through a U-shaped notch 65, as illustrated in FIG. 1D. In one embodiment, the test meter 10 (or 100) may include a second electrode connector 101, and first electrode connectors (102a, 102b), a test voltage unit 106, a signal measurement unit 107, a processor 212, a memory unit 210, and a visual display 202, as shown in FIG. 5. The first contact pad 67 may include two prongs denoted as 67a and 67b. In one exemplary embodiment, the first electrode connectors 102a and 102b separately connect to prongs 67a and 67b, respectively. The second electrode connector 101 may connect to second contact pad 63. The test meter 10 (or 100) may measure the resistance or electrical continuity between the prongs 67a and 67b to determine whether the test strip 62 is electrically connected to the test meter 100 (or 10).

In one embodiment, the test meter 10 (or 100) may apply a test voltage and/or a signal between the first contact pad 67 and the second contact pad 63. Once the test meter 10 (or 100) recognizes that the strip 62 has been inserted, the test meter 10 (or 100) turns on and initiates a fluid detection mode. In one embodiment, the fluid detection mode causes test meter 10 (or 100) to apply a constant signal of about 1 microampere between the first electrode 66 and the second electrode 64. Because the test strip 62 is initially dry, the test meter 10 (or 100) measures a relatively large voltage. When the fluid sample bridges the gap between the first electrode 66 and the second electrode 64 during the dosing process, the test meter 10 (or 100) will measure a decrease in measured voltage that is below a predetermined threshold causing test meter 10 (or 100) to automatically initiate the glucose test.

Figure 6A:
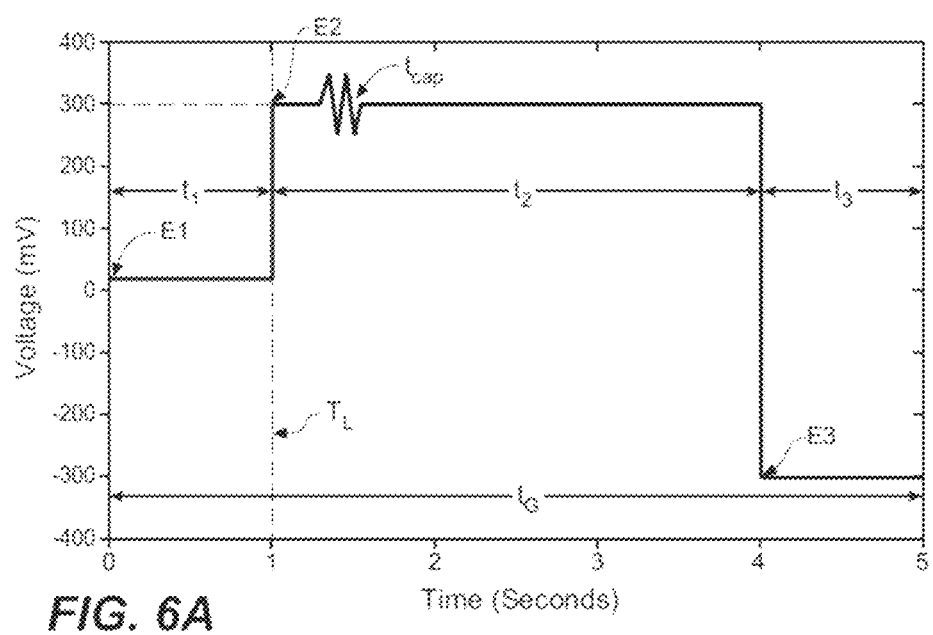
FIG. 6A shows an example of a tri-pulse potential waveform applied by the test meter of FIG. 5 to the working and counter electrodes for prescribed time intervals.

In one embodiment, the test meter 10 (or 100) may perform a glucose test by applying a plurality of test voltages for prescribed intervals, as shown in FIG. 6A. The plurality of test voltages may include a first test voltage E1 for a first time interval $t_1$, a second test voltage E2 for a second time interval $t_2$, and a third test voltage E3 for a third time interval $t_3$. The third voltage E3 may be different in the magnitude of the electromotive force, in polarity, or combinations of both with respect to the second test voltage E2. In the preferred embodiments, E3 may be of the same magnitude as E2 but opposite in polarity. A glucose test time interval $t_G$ represents an amount of time to perform the glucose test (but not necessarily all the calculations associated with the glucose test). Glucose test time interval $t_G$ may range from about 1 second to about 5 seconds from the start. Further, as illustrated in FIG. 6A, the second test voltage E2 may include a constant (DC) test voltage component and a superimposed alternating (AC), or alternatively oscillating, test voltage component. The superimposed alternating or oscillating test voltage component may be applied for a time interval indicated by $t_{cap}$.

The plurality of test signal values measured during any of the time intervals may be performed at a frequency ranging from about 1 measurement per microsecond to about one measurement per 100 milliseconds. While an embodiment using three test voltages in a serial manner is described, the glucose test may include different numbers of open-circuit and test voltages. For example, as an alternative embodiment, the glucose test could include an open-circuit for a first time interval, a second test voltage for a second time interval, and a third test voltage for a third time interval. It should be noted that the reference to "first," "second," and "third" are chosen for convenience and do not necessarily reflect the order in which the test voltages are applied. For instance, an embodiment may have a potential waveform where the third test voltage may be applied before the application of the first and second test voltage.

Once the glucose assay has been initiated, the test meter 10 (or 100) may apply a first test voltage E1 (e.g., approximately 20 mV in FIG. 6A) for a first time interval $t_1$ (e.g., 1 second in FIG. 6A). The first time interval $t_1$ may range from about 0.1 seconds to about 3 seconds and preferably range from about 0.2 seconds to about 2 seconds, and most preferably range from about 0.3 seconds to about 1 second.

Figure 6B:
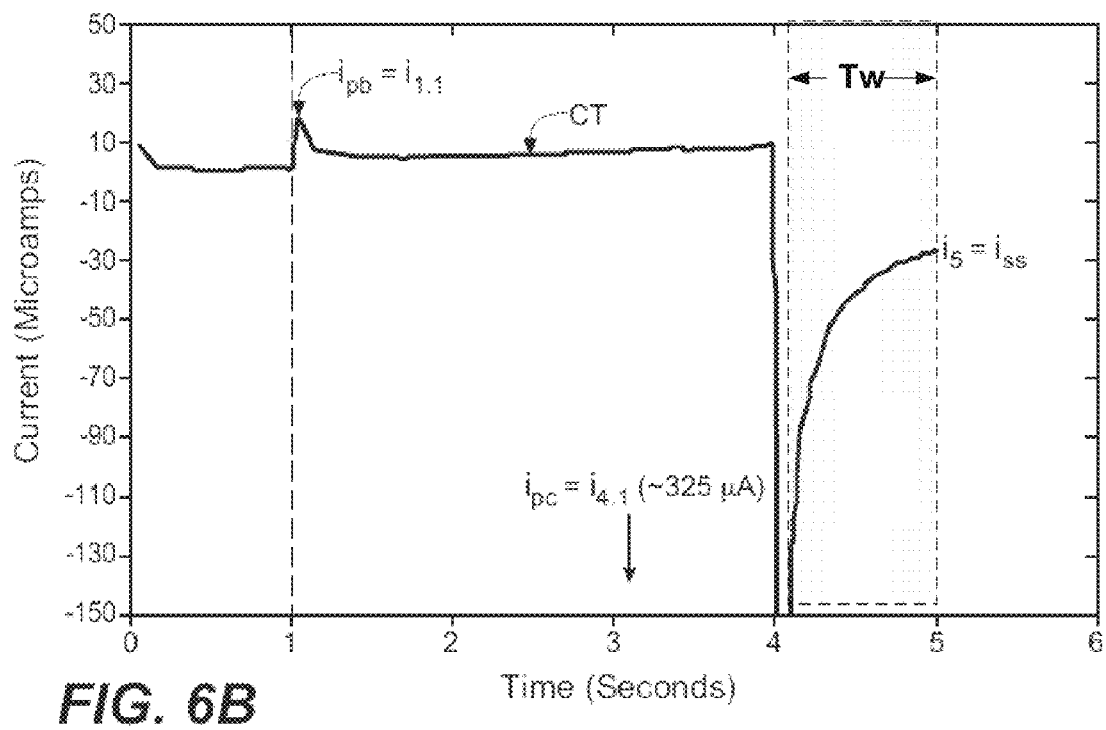
FIG. 6B shows an output signal transient CT generated testing a fluid sample.

The first time interval $t_1$ may be sufficiently long so that the sample-receiving chamber 61 may fully fill with sample and also so that the reagent layer 72 may at least partially dissolve or solvate. In one aspect, the first test voltage E1 may be a value relatively close to the redox potential of the mediator so that a relatively small amount of a reduction or oxidation signal is measured. FIG. 6B shows that a relatively small amount of signal is observed during the first time interval $t_1$ compared to the second and third time intervals $t_2$ and $t_3$. For example, when using ferricyanide and/or ferrocyanide as the mediator, the first test voltage E1 in FIG. 6A may range from about 1 mV to about 100 mV, preferably range from about 5 mV to about 50 mV, and most preferably range from about 10 mV to about 30 mV. Although the applied voltages are given as positive values in the preferred embodiments, the same voltages in the negative domain could also be utilized to accomplish the intended purpose of the claimed invention.

After applying the first test voltage E1, the test meter 10 (or 100) applies a second test voltage E2 between first electrode 66 and second electrode 64 (e.g., approximately 300 mVolts in FIG. 6A), for a second time interval $t_2$ (e.g., about 3 seconds in FIG. 6A). The second test voltage E2 may be a value sufficiently negative of the mediator redox potential so that a limiting oxidation signal is measured at the second electrode 64. For example, when using ferricyanide and/or ferrocyanide as the mediator, the second test voltage E2 may range from about zero mV to about 600 mV, preferably range from about 100 mV to about 600 mV, and more preferably is about 300 mV.

The second time interval $t_2$ should be sufficiently long so that the rate of generation of reduced mediator (e.g., ferrocyanide) may be monitored based on the magnitude of a limiting oxidation current. Reduced mediator is generated by enzymatic reactions with the reagent layer 72. During the second time interval $t_2$, a limiting amount of reduced mediator is oxidized at second electrode 64 and a non-limiting amount of oxidized mediator is reduced at first electrode 66 to form a concentration gradient between first electrode 66 and second electrode 64.

In an exemplary embodiment, the second time interval $t_2$ should also be sufficiently long so that a sufficient amount of ferricyanide may be generated or diffused at the second electrode 64. A sufficient amount of ferricyanide is required at the second electrode 64 so that a limiting current may be measured for oxidizing ferrocyanide at the first electrode 66 during the third test voltage E3. The second time interval $t_2$ may be less than about 60 seconds, and preferably may range from about 1 second to about 10 seconds, and more preferably range from about 2 seconds to about 5 seconds from the start. Likewise, the time interval indicated as $t_{cap}$ in FIG. 6A may also last over a range of times, but in one exemplary embodiment it has a duration of about 20 milliseconds. In one exemplary embodiment, the superimposed alternating test voltage component is applied after about 0.3 seconds to about 0.4 seconds after the application of the second test voltage E2, and induces a sine wave having a frequency of about 109 Hz with an amplitude of about +/−50 mV.

FIG. 6B shows a relatively small peak $i_{pb}$ after the beginning of the second time interval $t_2$ followed by a gradual increase of an absolute value of an oxidation current during the second time interval $t_2$. The small peak $i_{pb}$ occurs due to an initial depletion of reduced mediator after a transition from first voltage E1 to second voltage E2, referenced here as transition line $T_L$. Thereafter, there is a gradual absolute decrease in oxidation current after the small peak $i_{pb}$ is caused by the generation of ferrocyanide by reagent layer 72, which then diffuses to second electrode 64.

After applying the second test voltage E2, the test meter 10 (or 100) applies a third test voltage E3 between the first electrode 66 and the second electrode 64 (e.g., about −300 mVolts in FIG. 6A) for a third time interval $t_3$ (e.g., 1 second in FIG. 6A). The third test voltage E3 may be a value sufficiently positive of the mediator redox potential so that a limiting oxidation current is measured at the first electrode 66. For example, when using ferricyanide and/or ferrocyanide as the mediator, the third test voltage or signal E3 may range from about zero mV to about −600 mV, preferably range from about −100 mV to about −600 mV, and more preferably is about −300 mV.

The third time interval $t_3$ may be sufficiently long to monitor the diffusion of reduced mediator (e.g., ferrocyanide) near the first electrode 66 based on the magnitude of the oxidation current. During the third time interval $t_3$, a limiting amount of reduced mediator is oxidized at first electrode 66 and a non-limiting amount of oxidized mediator is reduced at the second electrode 64. The third time interval $t_3$ may range from about 0.1 seconds to about 5 seconds from the start and preferably range from about 0.3 seconds to about 3 seconds, and more preferably range from about 0.5 seconds to about 2 seconds.

FIG. 6B shows a relatively large peak $i_{pc}$ at the beginning of the third time interval $t_3$ followed by a decrease to a steady-state signal $i_{ss}$ value. In one embodiment, the second test voltage or signal E2 may have a first polarity and the third test voltage or signal E3 may have a second polarity that is opposite to the first polarity. In another embodiment, the second test voltage or signal E2 may be sufficiently negative of the mediator redox potential and the third test voltage E3 may be sufficiently positive of the mediator redox potential. The third test voltage or signal E3 may be applied immediately after the second test voltage or signal E2. However, one skilled in the art will appreciate that the magnitude and polarity of the second and third test voltages or signals may be chosen depending on the manner in which analyte concentration is determined.

A blood glucose concentration can be determined based on the test signal values. A first glucose concentration $G_1$ may be calculated using a glucose algorithm as shown in Equation 1:

$$G_1 = \left(\frac{|i_2|}{|i_3|}\right)^p (A|i_1| - z) \qquad \text{Eq. 1}$$

Where
  $i_1$ is a first output test signal value,
  $i_2$ is a second output test signal value,
  $i_3$ is a third output test signal value, and
  the terms A, p, and z can be empirically derived calibration constants.

All output test signal values (e.g., $i_1$, $i_2$, and $i_3$) in Equation 1 use the absolute value of the current. The first test signal value $i_1$ and the second test signal value $i_2$ can each be defined by an average or summation of one or more predetermined test signal values that occur during the third time interval $t_3$. The term $i_2$ is a second signal value that is based on a fourth signal value $i_4$, a fifth signal value $i_5$, and a sixth signal value $i_6$, which are all measured during a third time interval. The third test signal value $i_3$ can be defined by an average or summation of one or more predetermined test signal values that occur during the second time interval $t_2$. One skilled in the art will appreciate that names "first," "second," and "third" are chosen for convenience and do not necessarily reflect the order in which the signal values are calculated. A derivation of Eq. 1 can be found in U.S. Pat. No. 7,749,371, patented Jul. 6, 2010, which was filed on 30 Sep., 2005 and entitled "Method and Apparatus for Rapid Electrochemical Analysis," which is hereby incorporated by reference in its entirety into this application.

Referring now to FIGS. 6A and 6B, the peak signal (FIG. 6B) observed after the start (i.e., transition line $T_L$) of the second test potential time interval $t_2$ (FIG. 6A) may be denoted as $i_{pb}$, and the peak signal exhibited at the start of the third test potential time interval $t_3$ (FIG. 6A) may be denoted as $i_{pc}$. Equation 2 describes a relationship between the first signal transient CT and second signal transient CT when a test strip 62 is tested with a sample containing an interferent and "no" glucose.

$$i_{pc} - 2i_{pb} = -i_{ss} \qquad \text{Eq. 2}$$

Because there is typically "no" glucose in the sample during the first time period it is believed that the reagent layer 72 does not generate substantial amount of reduced mediator. Therefore, the signal transients would reflect only the oxidation of interferents. At the early time scale regime of around 1.0 seconds, it is assumed that reagent layer 72 does not generate a significant amount of reduced mediator because of the glucose reaction. Further, it is assumed that the reduced mediator which is generated will mostly remain near first electrode 66, where reagent layer 72 was initially deposited, and not significantly diffuse to second electrode 64. Therefore, the magnitude of $i_{pb}$ is predominantly ascribed to interferent oxidation at second electrode 64 which is a direct interferent current.

At a duration after the third voltage E3 has been provided to the strip (e.g., about −300 mV) at around 4.1 seconds, reagent layer 72 does generate a significant amount of reduced mediator at first electrode 66 in the presence of glucose because of the glucose reaction. A significant amount of reduced mediator can also be generated because of a possible oxidation of an interferent with the oxidized mediator. As mentioned earlier, interferent that reduces oxidized mediator contributes to a signal which may be referred to as an indirect current. In addition, interferents can also be oxidized directly at first electrode 66 which may be referred to as a direct current. For the situation in which the mediator can be oxidized at the working electrode, it may be assumed that the sum of the direct oxidation and indirect oxidation is approximately equal to a direct oxidation current that would have been measured if there was "no" oxidized mediator disposed on the working electrode. In summary, the magnitude of the $i_{pb}$ is ascribed to both indirect and direct interferent oxidation, and the glucose reaction at one of the first electrode 66 or second electrode 64. Because it has been determined that $i_{pb}$ is controlled mainly by interferents, $i_{pc}$ can be used with $i_{pb}$ together to determine a correction factor. For example, as shown below $i_{pb}$ can be used with $i_{pc}$ in a mathematical function to determine a corrected signal $i_{2(Corr)}$ which is proportional to glucose and less sensitive to interferents:

$$i_{2(CORR)} = i_2 \left[ \frac{i_{pc} - 2i_{pb} + i_{ss}}{i_{pc} + i_{ss}} \right] \qquad \text{Eq. 3}$$

Eq. 3 was empirically derived to calculate a signal $i_{2(Corr)}$ which is proportional to glucose and has a relative fraction of signal removed that is ascribed to interferents. The term $i_{ss}$ was added to both the numerator and denominator to allow the numerator to approach zero when "no" glucose is present. Determination of the steady-state signal $i_{ss}$ following application of the second electric potential is detailed in co-pending patent application Ser. No. 11/278,341, which is incorporated by reference into this application herein. Some examples of methods for calculating $i_{ss}$ can be found in U.S. Pat. Nos. 5,942,102 and 6,413,410, each of which is hereby incorporated by reference in its entirety.

Referring back now to Equation 1, Equation 3 can be represented in terms of $i_1$, $i_3$ and $i_2$ as based on signal measurements $i_4$, $i_5$, $i_6$, and $i_7$ as Equation 4:

$$i_2 = i_4 \left\{ \frac{i_5 - Fi_7 + Bi_6}{i_5 + Bi_6} \right\} \qquad \text{Eq. 4}$$

Where, as before, $i_2$ is a second signal value that is based on a fourth signal value $i_4$, a fifth signal value $i_5$, and a sixth signal value $i_6$ which are all measured during a third time interval $t_3$, and $i_7$ which in one embodiment is a seventh signal value measured in a first time interval $t_1$, and B and F are empirically derived constants. The time window for each signal measurement is discussed below.

This technique of accounting for the presence of interferents in an analyte can now be further refined to account for effects due to variation in temperature. In one example embodiment, $i_7$ may be the test signal value measured at an interval during a ramping from the first voltage E1 to the second voltage, which for convenience, has been designated as approximately 1.0 seconds into the test. While this ramped signal $i_7$ has been observed as a current change in an interval from the ramping of the first voltage E1 to the second voltage E2 at the transition line $T_L$, ramped signal $i_7$ may be measured at a time point within a suitable range as defined by a signal measured when the first voltage E1 is in the process of ramping to the second voltage E2 (from 0.7 second to near 1.1 second from the start in FIG. 6B) but not the signal measured once the first voltage E1 has been switched over completely to the second voltage E2, (after transition line $T_L$ or about 1.1 or more seconds in FIG. 6B). In the preferred embodiment and for ease of computational processing, applicants have selected ramped signal $i_7$ as the test signal measured at a test time equal to about 1.1 seconds into the signal transient caused by the change in voltages from E1 to E2, but it should be clear that the ramped signal $i_7$ may vary depending on the particular configurations of the relevant test strip.

Equation 4 can be modified to provide an even more accurate glucose concentration. Instead of using a simple average of summation of test signal values, the term $i_1$ can be defined to include peak signal values $i_{pb}$ and $i_{pc}$ and the steady-state signal $i_{ss}$, as shown in Equation 5, which is similar to Equation 3:

$$i_1 = i_2 \left\{ \frac{i_{pc} - 2i_{pb} + i_{ss}}{i_{pc} + i_{ss}} \right\} \qquad \text{Eq. 5}$$

where a calculation of the steady-state signal $i_{ss}$ can be based on a mathematical model, an extrapolation, an average at a predetermined time interval, a combination thereof, or any number of other ways for calculating a steady-state current.

Alternatively, $i_{ss}$ may be estimated by multiplying the test signal value at about 5 seconds from the start with a constant $K_8$ (e.g., 0.678). Thus, $i_{ss} \approx i(5)$ "×" $K_8$. The term $K_8$ can be estimated using Equation 6:

$$iss = \frac{i(5)}{1 + 4 \exp\left(\frac{-4\pi^2 D x 0.975}{L^2}\right)} \qquad \text{Eq. 6}$$

where the number 0.975 is about the time in seconds after the third test voltage or signal E3 is applied that corresponds to the signal at approximately 5 seconds for the particular embodiment of the strip 62, which, assuming a linear variation over the time between about 0.95 seconds and 1 second, is the average signal between 0.95 and 1 second, the term D is assumed to be about 5 "×" $10^{-6}$ $cm^2$/sec as a typical diffusion coefficient in blood, and the term L is assumed to be about 0.0095 cm, which represents the height of the spacer 60.

Turning again to Eq. 3, $i_{pc}$ may be the test signal value at about 4.1 seconds, and $i_{pb}$ may be the test signal value at about 1.1 second from the start, based on the test voltage or signal and test signal waveforms in FIGS. 6A and 6B.

Turning back to Eq. 1, $i_2$ may be defined to be $$i_2 = \sum_{t=4.4}^{5} i(t)$$

and $i_3$ may be defined to be $$i_3 = \sum_{t=1.4}^{4} i(t).$$

Equation 3 may be combined with Equations 1 and 2 to yield an equation for determining a more accurate glucose concentration that may compensate for the presence of endogenous and/or exogenous interferents in a blood sample, as shown in Equation 7:

$$G_1 = \left(\frac{i_2}{i_3}\right)^p \otimes \left(A \otimes i_2 \otimes \left\{\frac{i_{pc} - 2i_{pb} + i_{ss}}{i_{pc} + i_{ss}}\right\} - z\right) \quad \text{Eq. 7}$$

where the first glucose concentration $G_1$ is the output of the blood glucose algorithm and the terms A, p, and z are constants that may be derived empirically from manufacturing samples of the test strip.

The selection of the time intervals in which $i_1$, $i_3$ and $i_2$ may be calculated is described in co-pending Patent Application Publication No. 2007/0227912 entitled 'Methods and Apparatus for Analyzing a Sample in the Presence of Interferents', and methods for calibrating strip lots are described in U.S. Pat. No. 6,780,645, both of which are hereby incorporated by reference in their entirety into this application.

In the preferred embodiment, the glucose concentration $G_1$ of Equation 7 is determined by Equation 8 that utilizes signal $i_{2(Corr)}$, (which is proportional to glucose and has a relative fraction of signal removed that is ascribed to interferents):

$$G_1 = \left(\frac{|i_r|}{|i_l|}\right)^p (A | i_{2CORR} | -zgr) \quad \text{Eq. 8}$$

where:

$$i_r = \sum_{t=4.4}^{t=5} i(t);$$

$$i_l = \sum_{t=1.4}^{t=4} i(t);$$

$$i_{2(Corr)} = \left(\frac{|i_{pc}| + B|i_{ss}| - 2|i_{pb}|}{|i_{pc}| + b|i_{ss}|}\right) i_r \quad \text{Eq. 8.1}$$

Where
  $i_r$ is an output signal measured from about 4.4 seconds to about 5 seconds from the start;
  $i_l$ is an output signal measured from about 1.4 seconds to about 4 seconds from the start; and for the embodiment here, $i_{2(Corr)}$ of Equation 8.1 can be replaced with Equation 8.2:

$$i_{2(Corr)} = \left(\frac{|i_{4.1secs}| + B|i_{5\ secs}| - C|i_{1.1seconds}|}{|i_{4.1seconds}|B|i_{5seconds}|}\right) i_r \quad \text{Eq. 8.2}$$

A, B, C, p, and zgr are manufacturing parameters.

For the embodiments described here, A is approximately 0.192, B is approximately 0.68, C is approximately 2, p is approximately 0.52, and zgr is approximately 2.

In my research into bias or error in the signal transient for this particular analyte system, my presumption is that a transient decaying too fast may result in extreme low bias. As the absolute signal is tied to glucose concentration it cannot be an indicator of error trigger leading to low bias at all glucose concentration within system range. Therefore, a derivative approach should be pursued. Such an effort, however, is usually linked to curve fitting or other computationally intensive processes. Further, I believe that there is a specific transient shape, which will always lead to a negatively biased result. This mode features a shallow transient decay. Unfortunately, this mode cannot be identified by an absolute signal measurement, as this is modulated by the analyte concentration itself (e.g., glucose).

Figure 8:
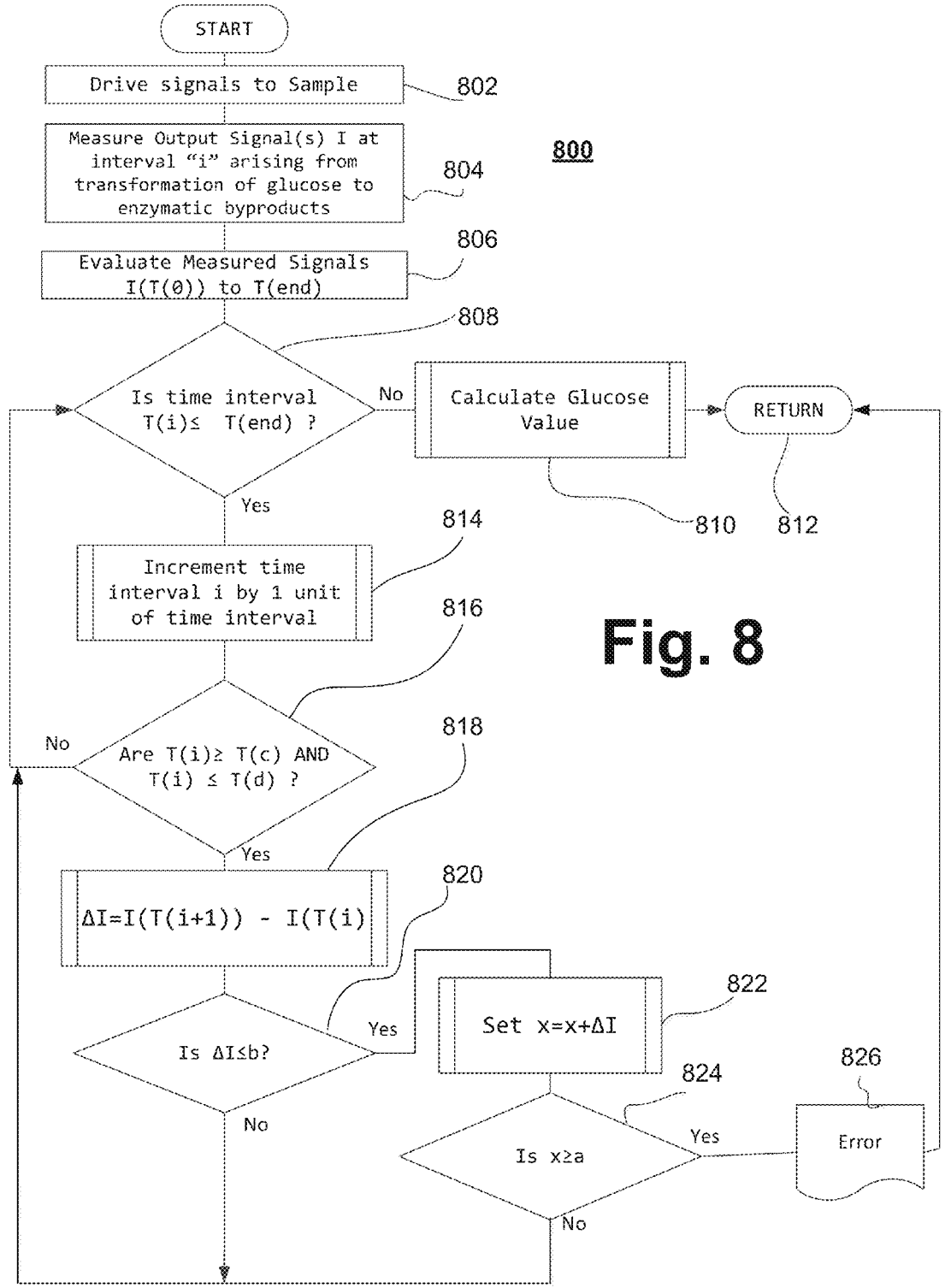
FIG. 8 illustrates a logic diagram in the techniques devised by the inventors to detect the error during a glucose measurement process.

The technique that I have devised here (FIG. 8) works with very low processing demands as it only retains the difference of consecutive points with a cumulative sum. Consequently, the technical contributions or effects of my technique include the ability to let the user know if the measurement test is defective quicker than before. Another technical contribution by my technique is that it prevents specific errors within the signal to skew the end result. This ensures that the computed analyte concentration result returned by the system is likely to adhere to the accuracy standard as described by the manufacturer. Yet a further technical advantage is that this error mode may be filtered effectively with very little effort, as "no" fitting of a shape is required. Programming within a hand-held, low-cost meter is easy without a need to increase processing resource.

Accordingly, I have configured microcontroller 38 (which is coupled to a power source, memory and the plurality of electrodes of the biosensor 62) so that the microcontroller is programmed with logic process 800 (FIG. 8) to drive a signal, at step 802, to the at least two electrodes (e.g., 10, 12, 14) when a fluid sample with an glucose is deposited proximate the at least two electrodes to start a test measurement sequence (FIGS. 6A and 6B) for an electrochemical reaction of the glucose in the fluid sample with the reagent on the biosensor. The microcontroller 38 measures, at step 804, an output signal (in the form of current output I(T)(i)) from at least one electrode during the electrochemical reaction over a series of time intervals T(i) to obtain a magnitude of the output signal for each time interval i. At step 806, the microcontroller 38 evaluates all of the measured or sampled signals I(T(i)) from the beginning of the test window Tw to the end of the test sequence. The evaluation 806 starts with a query at step 808 to determine if the evaluation is completed. If the query 808 returns a "no", meaning that the time interval T for which the output signal I being evaluated is greater than the end of the test window Tw (which can be from 2 to 15 seconds after test start time) then the controller moves to step 810 calculate the glucose value at step 810. At step 812, the controller will, depending on the prior step (810 or 826), will annunciate the glucose value or an indication of an error in the measurement signals. If the query 808 returns a "yes"; meaning that the time interval T for which the output signal is being evaluated is less than the test end time, then the controller increments the sampling interval at step 816 to the next time interval in its evaluation of the output signal. At step 816, the controller 38 evaluates the current time point at which the output signal is being evaluated to ensure that the current time point is within a window from the start time to the end time. If the query at step 816 returns a "no" then the controller returns to step 808, otherwise if the query 816 returns a yes, meaning that the time interval for which the measured output signal is being evaluated is within this window, the controller determines, at step 818 an output differential ΔI as a difference in the respective magnitudes of the output signal for at least two consecutive time intervals i and i+1 within a predetermined time window Tw (FIG. 6B) from the start to the end of the test measurement sequence.

At step 820, if the output differential ΔI is greater than zero then the microcontroller 38 increments index "x" by the output differential Δ1, i.e., x=x+ΔI. At query step 824, if the index "x" is greater or equal to a predetermined value "a" then controller moves to step 826 to flag or annunciate an error. Otherwise, if the query at step 824 returns a "no" (i.e., x<a) then the system returns to step 808 to determine if the time period is outside the time window from the start of the test sequence to the end of the test sequence time interval. If query 808 returns a true or "yes" then the system calculates (described earlier) the glucose value from the output signal at step 810 and at step 812 returns to the main routine and annunciate the glucose measurement or value as determined from Equations 8 through 8.2. Assuming that the query at 824 returns a "no" then there is no error in the output signal(s) of the electrodes and the system may annunciate the glucose measurement calculated from step 810.

As implemented, my technique provides a technical contribution or technical effect to the art in that it takes as little resource as possible from the microcontroller—only four parameters need to be introduced ('a', 'b' along with window start time 'c' and end time 'd' of the test sequence) and one variables retained and updated ('x'). For the system utilizing strip 62, Table 1 provides the range of parameters for such system in the utilization of logic process 800 of FIG. 8.

TABLE 1

| Parameters | |
| --- | --- |
| Parameter | System |
| a | ≈2 microamps |
| b | ≈0.5 microamps |
| c (Window Start Time of Tw) | ≈4.2 seconds from start of test sequence |
| d (Window End Time of Tw) | ≈5 seconds from start of test sequence |

My technique described here is the simplest possible, meaning implementation on the meter takes as little resource as possible—only four parameters need to be introduced ('a', 'b', 'c' & 'd') and two variables retained and updated (i.e., 'x' & 'y'). Parameter 'a' describes the total sum of signal points necessary to trigger the error (which equates to sum area). Parameter 'b' defines the difference of consecutive measurement points (current signal output point minus last point) necessary to be counted by the algorithm. Parameters 'c' and 'd' define the time window in which the error has to occur to merit an error trigger (where 'c' is the start time, 'd' is the end time). Only if both conditions are satisfied (i.e., the sum of signal differences within the specified time window Tw), the error is triggered. This makes my technique scalable, which in turns allows finding an appropriate balance between true positives (i.e., transients which trigger the trap, and lead to an inaccurate result) and false positives (i.e., output transients which trigger the trap, yet lead to an accurate result).

Figure 7B:
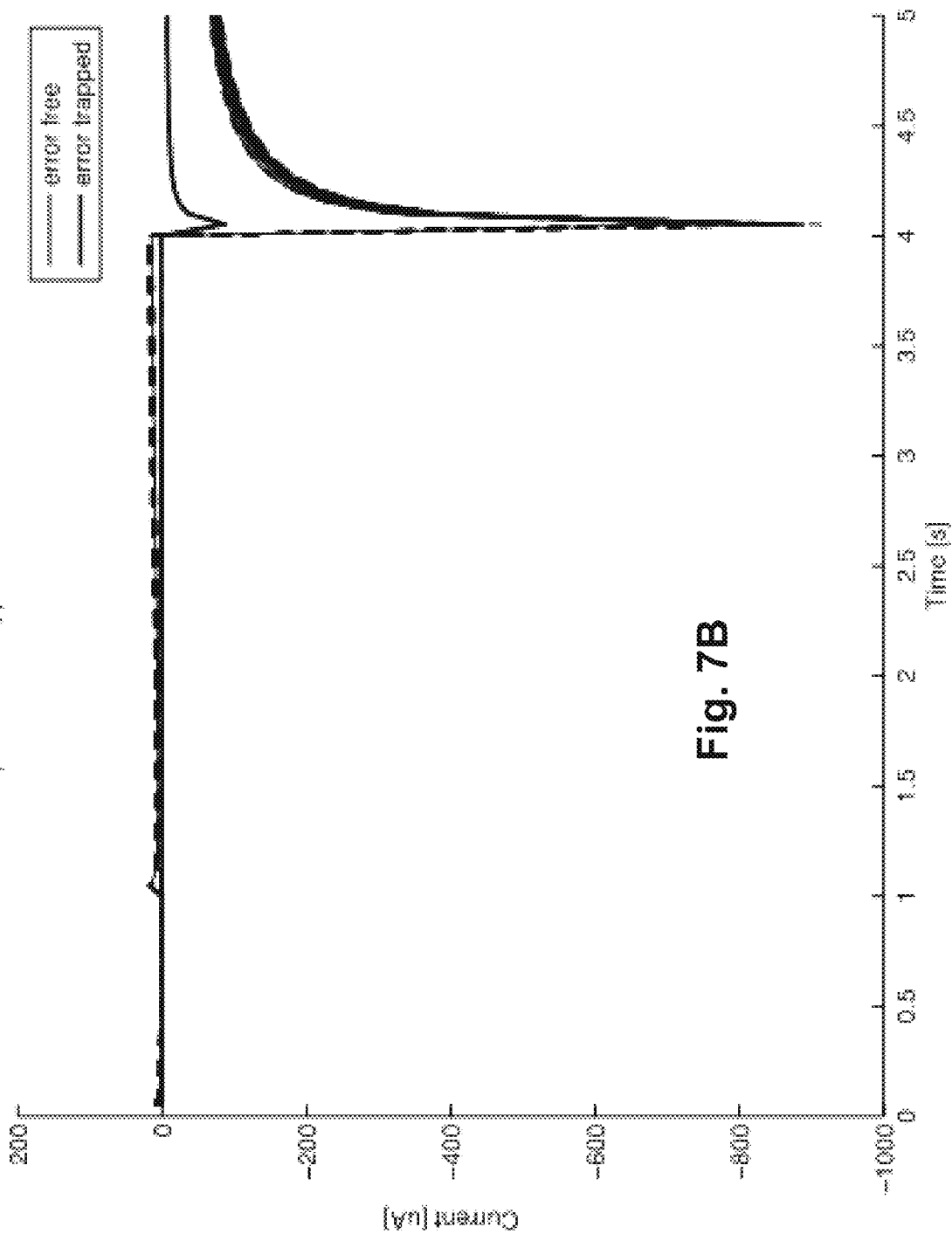
FIG. 7B illustrates a comparison between normal and erroneous signal transients.
Figure 7C:
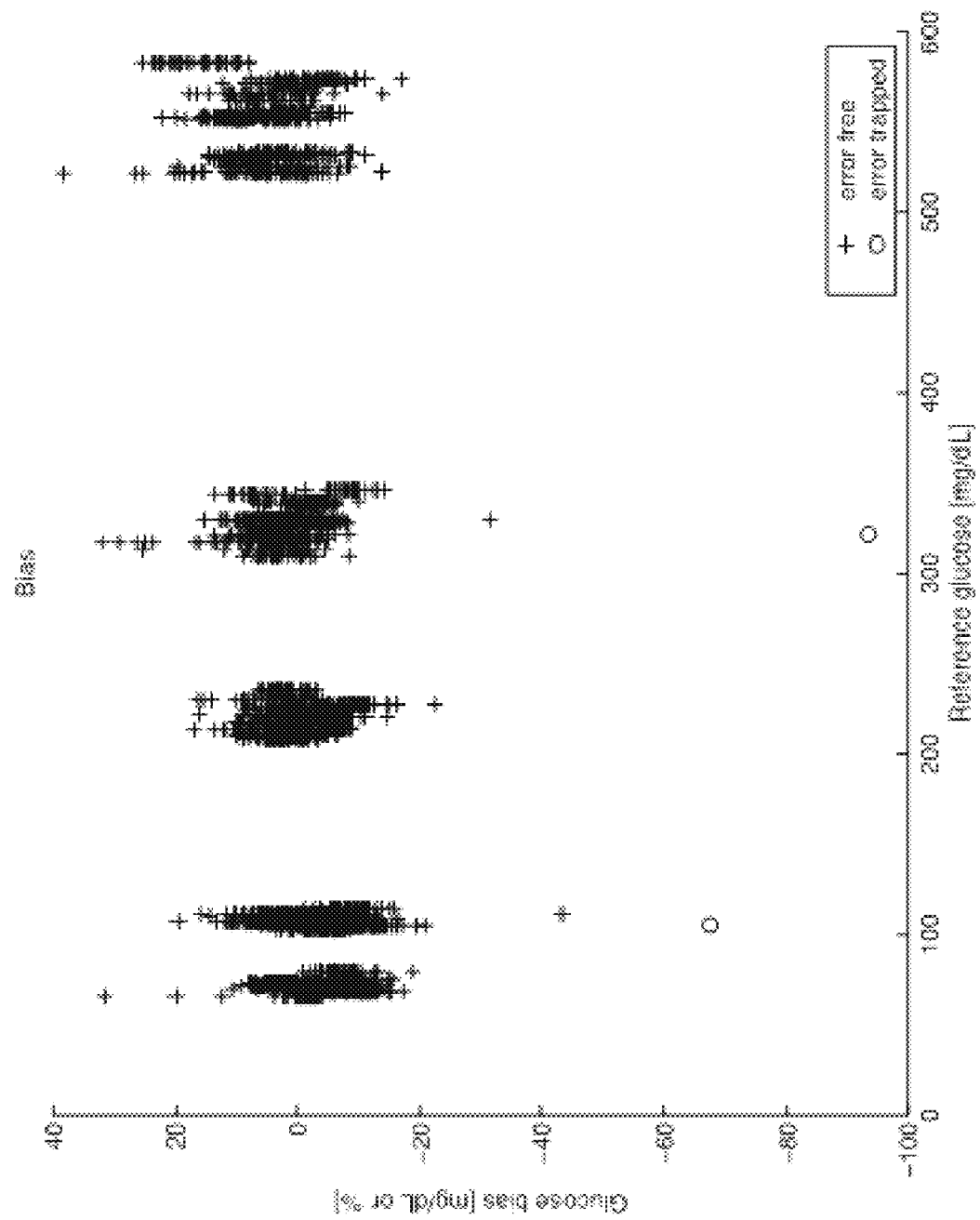
FIG. 7C illustrates the large bias for a glucose measurement at 100 mg/dL.

FIG. 7A illustrates some of the transients identified by my technique. Two out of 2970 transients were identified as erroneous (equates to 0.067%). FIG. 7B shows the difference of the erroneous transients to normal transients generated by the same large blood sample. Each of the errors picked up would have contributed to a bias in excess of −65% (based on the glucose calculation described herein), as shown in FIG. 7C. Of the 2970 transients featuring in FIGS. 7A and 7B, only two of the signal output transients are true positives and none are false positives.

While the invention has been described in terms of particular variations and illustrative figures, those of ordinary skill in the art will recognize that the invention is not limited to the variations or figures described. In addition, where methods and steps described above indicate certain events occurring in certain order, it is intended that certain steps do not have to be performed in the order described but in any order as long as the steps allow the embodiments to function for their intended purposes. Therefore, to the extent there are variations of the invention, which are within the spirit of the disclosure or equivalent to the inventions found in the claims, it is the intent that this patent will cover those variations as well.

What is claimed is:

1. A glucose measurement system comprising:
    a biosensor having a plurality of electrodes including at least two electrodes with a reagent disposed thereon; and
    a meter including:
        a microcontroller coupled to a power source, memory and the plurality of electrodes of the biosensor and in which the microcontroller is configured to:
        drive a signal to the at least two electrodes when a fluid sample having glucose is deposited proximate the at least two electrodes to start a test measurement sequence for an electrochemical reaction of the glucose in the fluid sample with the reagent;
        measure an output signal from at least one electrode during the electrochemical reaction over a series of time intervals to obtain a magnitude of the output signal for each time interval;
        determine an output differential as a difference in the respective magnitudes of the output signal for at least two consecutive time intervals within a predetermined time window during the test measurement sequence;
        if the output differential is greater than a predetermined threshold then increment an index value as equal to the sum of both a previous value of the index and the output differential and if the index is greater or equal to a predetermined index value then annunciate an error otherwise calculate the glucose value from the output signal and annunciate the glucose value.

2. The system of claim 1, in which the predetermined time window comprises from about 1 second after a start of a test sequence to about 8 seconds after the start of the test sequence.

3. The system of claim 1, in which the predetermined index value comprises about 5 and the predetermined threshold comprises about 300.

4. The system of claim 1, in which the predetermined time window comprises from about 2 second after a start of a test sequence to about 8 seconds after the start of the test sequence.

5. The system of claim 1, in which the predetermined index value comprises about 5 and the predetermined threshold comprises about 150.

6. A method of determining a glucose value from a fluid sample with a biosensor having at least two electrodes and reagent disposed thereon and a glucose meter having a microcontroller configured to connect to the biosensor and to a memory and a power source, the method comprising the steps of:
  initiating a start of a test measurement sequence upon deposition of a fluid sample proximate the at least two electrodes of the biosensor;
  applying an input signal to the fluid sample to cause a transformation of glucose into an enzymatic by-product;
  measuring output signal transient from the fluid sample over a predetermined time window from the start of the test sequence, the measuring including sampling an output signal from at least one electrode during the electrochemical reaction over a series of time intervals to obtain a magnitude of the output signal for each time interval;
  determining an output differential as a difference in the respective magnitudes of the output signal for at least two consecutive time intervals within the predetermined time window during the test measurement sequence;
  if the output differential is greater than zero then setting an index value as equal to the sum of both a previous value of the index and the output differential, otherwise if the index is greater than a predetermined index value then annunciating an error, otherwise calculating a glucose value of the fluid sample and annunciating the glucose value.

7. The method of claim 6, in which the calculating of the glucose value comprises measuring a magnitude of the output signal proximate a predetermined time interval from the start of the test sequence and utilizing an equation of the form:

$$G_1 = \left(\frac{|i_r|}{|i_l|}\right)^p (A|i_{2CORR}| - zgr)$$

where:
  $G_1$ comprises a glucose measurement value;

$$i_r = \sum_{t=4.4}^{t=5} i(t); \quad i_l = \sum_{t=1.4}^{t=4} i(t);$$

$$i_{2(Corr)} = \left(\frac{|i_{4.1secs}| + B|i_{5\ secs}| - C|i_{1.1seconds}|}{|i_{4.1seconds}|B|i_{5seconds}|}\right)i_r$$

$i_r$ is an output signal measured from about 4.4 seconds to about 5 seconds from the start;
  $i_l$ is an output signal measured from about 1.4 seconds to about 4 seconds from the start; and
  A, B, C, p, and zgr are manufacturing parameters in which A is approximately 0.19, B is approximately 0.68, C is approximately 2, p is approximately 0.52, and zgr is approximately 2.

8. The method of claim 6, in which the predetermined time window comprises from about 1 second after a start of a test sequence to about 8 seconds after the start of the test sequence.

9. The method of claim 6, in which the predetermined index value comprises about 2 microamps and the predetermined threshold comprises about 0.5 microamps.

10. The method of claim 6, in which the predetermined time window comprises from about 2 seconds after a start of a test sequence to about 8 seconds after the start of the test sequence.

* * * * *